(12) United States Patent
Meislin

(10) Patent No.: US 6,491,692 B1
(45) Date of Patent: Dec. 10, 2002

(54) CARTILAGE BRUSH AND METHOD

(76) Inventor: Robert Meislin, 8 Ben Azai St, Jerusalem 93505 (IL)

( * ) Notice: Subject to any disclaimer, the term of this patent is extended or adjusted under 35 U.S.C. 154(b) by 198 days.

(21) Appl. No.: 09/641,515

(22) Filed: Aug. 21, 2000

(51) Int. Cl.[7] .................................................. A61F 5/04
(52) U.S. Cl. ......................... 606/53; 600/569; 15/22.2; 15/23
(58) Field of Search .................. 606/53, 171; 600/569; 15/22.1, 22.2, 23

(56) References Cited

U.S. PATENT DOCUMENTS

| | | | | |
|---|---|---|---|---|
| 3,379,906 A | * | 4/1968 | Spohr | |
| 4,630,326 A | * | 12/1986 | Stevens | |
| 5,370,653 A | * | 12/1994 | Cragg | 606/170 |
| 5,496,338 A | * | 3/1996 | Miyagi et al. | 606/162 |
| 5,535,756 A | * | 7/1996 | Parasher | |
| 5,699,575 A | * | 12/1997 | Peifer | 15/23 |
| 5,738,575 A | * | 4/1998 | Bock | 433/216 |
| 5,809,601 A | * | 9/1998 | Rivera | 15/23 |
| 5,882,329 A | * | 3/1999 | Patterson et al. | 604/49 |
| 5,895,400 A | * | 4/1999 | Abela | 606/159 |
| 5,899,850 A | * | 5/1999 | Ouchi | 600/104 |
| 6,093,155 A | * | 7/2000 | Ouchi | 600/569 |
| 6,371,934 B1 | * | 4/2002 | Jackson et al. | 604/35 |

* cited by examiner

*Primary Examiner*—Ralph A. Lewis
(74) *Attorney, Agent, or Firm*—Craig Weiss; Jeffrey Weiss; Weiss, Moy & Harris, P.C.

(57) ABSTRACT

A cartilage fragment removal device and method permits the removal of articular cartilage fragments, without undue risk of harm to the healthy cartilage surface. The device consists of a brush attachment located at the end of a shaft, which shaft is in turn coupled to a drive mechanism. The drive mechanism imparts a desired brushing motion to the brush attachment, the bristles of which are brought into contact with the articular cartilage fragment during an arthroscopic procedure so as to cause the fragment's removal. The removed fragment is then suctioned from the joint cavity, preferably using a suction tube that is integral to the cartilage fragment removal device.

18 Claims, 1 Drawing Sheet

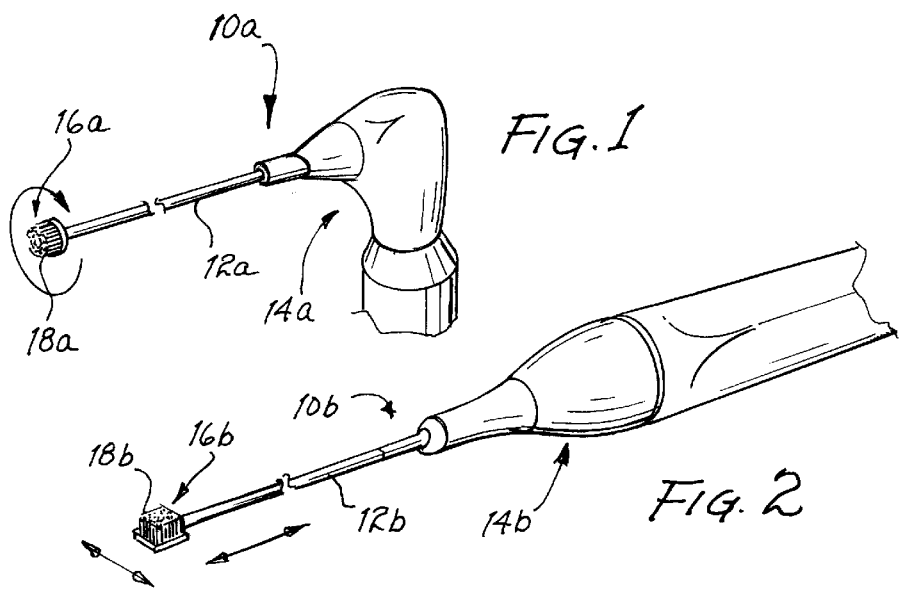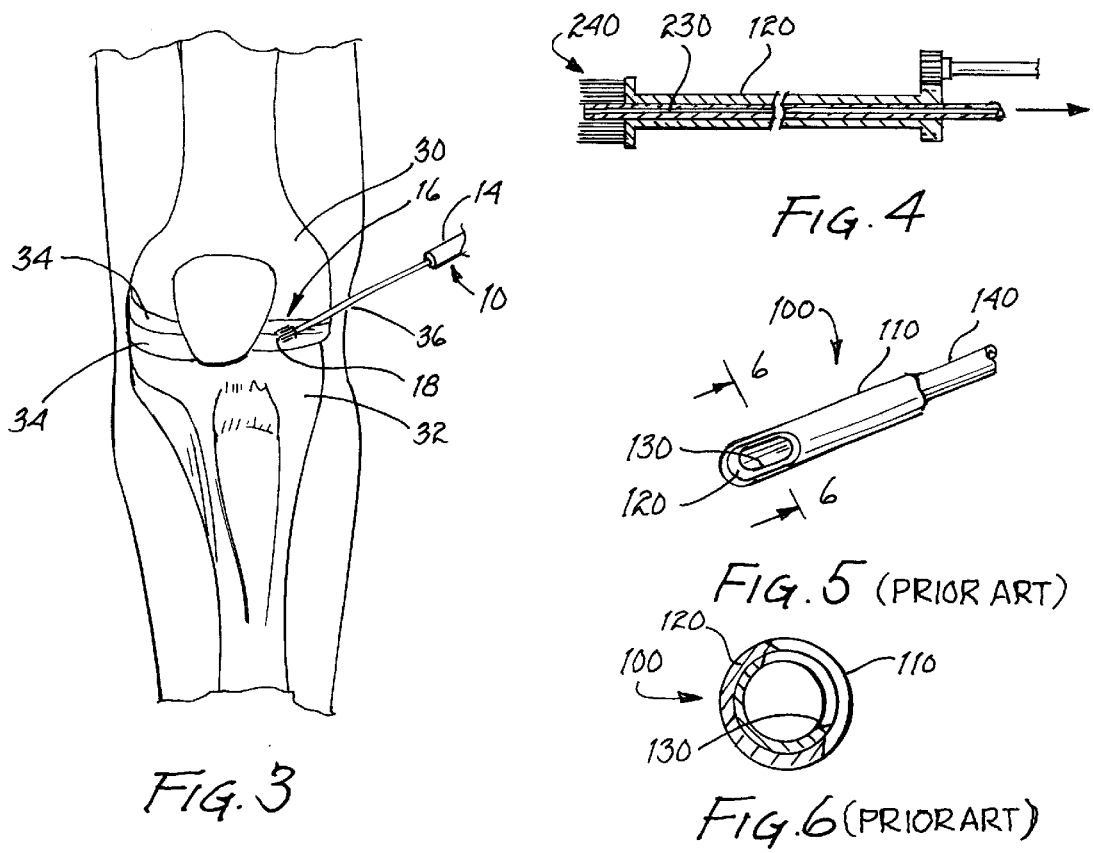

CARTILAGE BRUSH AND METHOD

BACKGROUND OF THE INVENTION

1. Field of the Invention

This invention relates to articular cartilage repair generally and, more particularly, to a device and method for removing loose articular cartilage fragments during an arthroscopic procedure with a reduced risk of damage to healthy cartilage.

2. Description of the Prior Art

Diarthroses in the human body, freely movable joints, are distinguished by, among other things, the presence of articular cartilage on the surfaces of the articulating bones. The articular cartilage does not bind the bones together; instead, it acts to reduce friction when the bones move and helps to absorb shock. There are a number of different types of diarthroses, including gliding, hinge, pivot, condyloid, saddle, and ball and socket. The two major diarthroses are the knee and the shoulder joints.

With specific regard to the knee joint, the surfaces where the femur, tibia and patella touch are all covered with articular cartilage. As a result of excess stress on the joint, trauma, muscle weakness, or perhaps other factors, a fragment (or fragments) of articular cartilage may partially dislodge from the articular cartilage surface—so that it extends into the joint cavity but is still partially attached to the cartilage surface. Such loose cartilage fragments can be sources of clicking, catching, or popping in the joint—and/ or can cause pain, swelling or other mechanical irritation. While the knee joint is provided as an example, it should be understood that the problem of articular cartilage occurs in the shoulder and other diarthroses in the body as well.

Loose cartilage fragments can be removed during an arthroscopic surgical procedure. One prior art device for the removal of loose fragments is an arthroscopic surgery blade made by Smith & Nephew, Inc. The Smith & Nephew blade is a rotary vacuum shaver, having an external stationary tube having a sidefacing opening at its distal end, and an internal rotating blade. When the opening is brought in contact with the loose cartilage fragments, the rotating blade shears the fragment, which may then be suctioned through the instrument and out of the joint cavity.

One significant drawback to the Smith & Nephew device, however, is that during operation the blade can nick or cut healthy articular cartilage or can inadvertently remove healthy cartilage with the fragment—undermining the healthy cartilage surface.

A need therefore existed for a device and method for removing articular cartilage fragments from a joint, with a reduced risk of undermining the healthy cartilage surface. The articular cartilage brush and method of the present invention provides these and other related advantages.

SUMMARY OF THE INVENTION

It is an object of this invention to provide an improved device and method for removing articular cartilage fragments from any body joint with a reduced risk of undermining the healthy cartilage surface.

It is a further object of this invention to provide an improved device and method for removing articular cartilage fragments from the knee joint with a reduced risk of undermining the healthy cartilage surface.

BRIEF DESCRIPTION OF THE PREFERRED EMBODIMENTS

In accordance with one embodiment of the present invention, an improved cartilage fragment removal device is disclosed. The device comprises, in combination: a shaft having a proximal end and a distal end and dimensioned to be inserted into an incision of the size made for insertion of surgical instruments during arthroscopic surgery; a brush attachment having a plurality of bristles thereon coupled to the distal end of the shaft; and drive means coupled to a proximate end of the shaft for driving the brush attachment.

In accordance with a further embodiment of the present invention, a method for removing articular cartilage fragments comprising the steps of: providing a cartilage fragment removal device comprising: a shaft having a proximal end and a distal end and dimensioned to be inserted into an incision of the size made for insertion of surgical instruments during arthroscopic surgery; a brush attachment having a plurality of bristles thereon coupled to the distal end of the shaft; and drive means coupled to a proximate end of the shaft for driving the brush attachment; making an incision in a portion of a body for permitting access to an area having an articular cartilage fragment to be removed; inserting into the incision the brush attachment; driving the brush attachment; bringing the brush attachment in a driving condition into contact with the articular cartilage fragment to be removed until the articular cartilage fragment is detached; and removing the detached articular cartilage fragment from the body.

BRIEF DESCRIPTION OF THE DRAWINGS

FIG. 1 is a perspective view of an embodiment of the cartilage fragment removal device of the present invention.

FIG. 2 is a perspective view of another embodiment of the cartilage fragment removal device of the present invention.

FIG. 3 is a front view of a cartilage fragment removal device of the present invention being used on an articular cartilage surface in the knee joint.

FIG. 4 is a side, cross-sectional view of another embodiment of the cartilage fragment removal device of the present invention.

FIG. 5 is a perspective view of a prior art cartilage fragment removal device.

FIG. 6 is a cross-sectional view of the prior art cartilage fragment removal device of FIG. 5, taken along line 6—6.

DESCRIPTION OF THE PREFERRED EMBODIMENTS

Referring first to FIGS. 5 and 6, the prior art Smith & Nephew cartilage removal device (hereinafter"Smith & Nephew device 100") is shown. The Smith & Nephew device 100 has an external stationary tube 110 with a side-facing opening 120 at its distal end, and an internal rotating blade 130 at the end of a cannula 140. When the opening 120 is brought in contact with loose cartilage fragments, the rotating blade 130 shears the fragment, which may then be suctioned through the cannula 140 and out of the joint cavity. In use, the rotating blade 130 can inadvertently nick or cut the healthy cartilage surface proximate the area where the fragment is attached.

Referring to FIGS. 1 and 2, reference numbers 10a and 10b refer to two embodiments of the cartilage fragment removal device (referred to generically as the cartilage fragment removal device 10) of the present invention. The cartilage fragment removal device 10a generally comprises a shaft 12a (referred to generically as a shaft 12), coupled at first end to a driver 14a (referred to generically as a driver 14) and at a second end to a brush attachment 16a (referred to generically as a brush attachment 16). The brush attachment 16a has a plurality of bristles 18a (referred to generically as bristles 18) thereon. The cartilage fragment removal device 10b generally comprises a shaft 12b, coupled at first end to a driver 14b and at a second end to a brush attachment 16b. The brush attachment 16b has a plurality of bristles 18b thereon.

Referring specifically to FIG. 1, the brush attachment 16a has bristles 18a positioned thereon in a circular arrangement. The bristles 18 may be comprised of any desired material having sufficient strength to detach articular cartilage fragments upon activation of the cartilage fragment removal device 10, yet not so abrasive as to damage healthy articular cartilage when the bristles 18, in motion, are brought into contact with such cartilage. Exemplary materials can include nylon, plastic, and the like. The bristles 18 must also be rooted to the brush attachment 16 with sufficient strength so as not to become detached during operation, and potentially left in the joint cavity.

The brush attachment 16 and shaft 12 should be dimensioned to be insertable into an incision of the type and size typically made for the insertion of surgical instruments used during arthroscopic surgery, including arthroscopes, cannulas, prior art cartilage fragment removal devices, repair devices, etc. Preferably, the diameter of the brush attachment 16a would be in the range of from about 3.5 millimeters to about 5.5 millimeters, with different sizes available depending on the joint in which the device is to be used, the size of the fragment to be removed, and other considerations.

The driver 14 may be an electric motor or other drive mechanism, coupled to the brush attachment 16 through the shaft 12 in such manner so as to impart to the brush attachment 16 the desired brushing motion. (Optionally, the driver 14 could simply be a manual drive force supplied by the surgeon or other attending health care professional who imparts the desired brushing motion in a manner like that in which a person using a manual toothbrush can apply any desired brushing motion, as necessary.) As shown in FIG. 1, the brush attachment 16a is moved in a circular motion by the driver 14a.

Referring now to FIG. 2, another embodiment of the cartilage fragment removal device 10 of the present invention is shown. The cartilage fragment removal device 10b has a brush attachment 16b with bristles 18b positioned thereon in a foursided, preferably rectangular arrangement. In this embodiment, and unlike the embodiment of FIG. 1, the bristles are at a ninety degree angle relative to the shaft 12b. It may also be preferable, for some uses, to provide a cartilage fragment device 10 having a brush attachment 16 at an angle orientation other than what is shown in FIGS. 1 or 2, e.g., at a forty-five degree angle relative to the shaft 12. Optionally, the shaft 12 (or at least a portion thereof proximate the brush attachment 16) or the brush attachment 16 itself may be made of flexible material so as to permit adjustment of the orientation of the brush attachment 16 during use.

While four-sided and circular arrangements of bristles 18 are shown, it would be possible to provide other arrangements of the bristles 18, including for example oval, triangular, and other configurations, without departing from the spirit or scope of the present invention.

The driver 14b, which in this embodiment is on the same axis as the shaft 12b but which could alternatively be arrayed at an angle thereto as in FIG. 1, may be an electric motor or other drive mechanism, coupled to the brush attachment 16b through the shaft 12b in such manner so as to impart to the brush attachment 16b the desired brushing motion. As shown in FIG. 2, the brush attachment 16b/driver 14a may be coupled so as to impart a side to side or back and forth oscillating motion, as desired.

Referring now to FIG. 4, another embodiment of the cartilage fragment removal device 10 of the present invention is shown. In this embodiment, a shaft 220 has a suction tube 230 therethrough, which suction tube 230 has an opening in a brush attachment 240 at a distal end of the shaft 220. When a cartilage fragment is removed using the brush attachment 240, the removed fragment may then be suctioned out of the joint cavity through the suction tube 230. The use of a suction tube 230 as an integral part of the cartilage fragment removal device 10 is possible with any disclosed embodiments of the device including the cartilage fragment removal device 10a and 10b. As an alternative to the positioning of a suction tube 230 within the shaft 220, the suction tube 230 could be separate from the cartilage fragment removal device and could be separately inserted into the joint cavity through a second incision.

Referring now to FIG. 3, a front view of a cartilage fragment removal device 10 of the present invention is shown being used on an articular cartilage surface in the knee joint. While the knee joint is herein illustrated, it should be understood that the cartilage fragment removal device of the present invention may be used in any body joint having an articular cartilage surface wherein a cartilage fragment is present and requires removal.

As shown in FIG. 3, the joint surfaces of the femur 30 and tibia 32 are each covered with an articular cartilage surface 34. The cartilage fragment removal device 10 is inserted through an incision 36 proximate the joint cavity, so as to enable the positioning of the brush attachment portion 16 proximate the articular cartilage fragment to be removed. The positioning of the brush attachment portion 16 is guided by the surgeon using an arthroscope (not shown)—until the bristles 18 on the brush attachment 16 are in contact with the articular cartilage fragment. Either before or after contact has been made, the driver 14 is activated, imparting the desired brushing motion to the brush attachment 16—either circular, oscillating from side to side, oscillating back and forth, some combination of these motions or some other desired brushing motion. The bristles 18, in motion, remain in contact with the articular cartilage fragment until that fragment has been detached from the healthy, surrounding articular cartilage surface. The fragment is then suctioned from the joint cavity, using either a separate suction tube (not shown) inserted into the joint cavity through a second incision, or through the suction tube 230 (see FIG. 4).

Because the bristles 18 when in motion will not damage healthy articular cartilage, the cartilage fragment removal device 10 may also be used to conduct a general cleaning of the articular cartilage surface, so as to ensure that all fragments have been removed—including ones that may not visible with the arthroscope. Indeed, such a cleaning can be made part of a standard arthroscopic procedure.

It should be noted that the brush attachment 16 and the shaft 12 are preferably disposable, with the driver 14 dimensioned to release the shaft 12 after a single use and accept a replacement shaft 12 for the next use.

While the invention has been particularly shown and described with reference to preferred embodiments thereof, it will be understood by those skilled in the art that the foregoing and other changes in form and details may be made therein without departing from the spirit and scope of the invention.

What is claimed is:

1. An improved cartilage fragment removal device comprising, in combination;
   a rigid shaft having a proximal end and a distal end and dimensioned to be inserted into an incision of the size made for insertion of surgical instruments during arthroscopic surgery;
   a brush attachment having a plurality of bristles thereon coupled to said distal end of said rigid shaft, said brush attachment having a diameter within a range of about 3.5 millimeters to about 5.5 millimeters; and
   drive means coupled to a proximate end of said rigid shaft for driving said brush attachment to remove cartilage fragments.

2. The improved cartilage fragment removal device of claim 1 wherein said bristles are arranged in a substantially circular orientation.

3. The improved cartilage fragment removal device of claim 1 wherein said bristles are arranged in a substantially foursided orientation.

4. The improved cartilage fragment removal device of claim 3 wherein said bristles are arranged in a substantially rectangular orientation.

5. The improved cartilage fragment removal device of claim 1 wherein said bristles extend at a substantially ninety degree angle from said shaft.

6. The improved cartilage fragment removal device of claim 1 wherein said bristles extend parallel to an axis of said shaft.

7. The improved cartilage fragment removal device of claim 1 further comprising a suction conduit having a proximal end and distal end wherein said distal end is proximate said brush attachment.

8. The improved cartilage fragment removal device of claim 1 wherein said drive means is adapted to drive said brush attachment in a rotary motion.

9. The improved cartilage fragment removal device of claim 1 wherein said drive means drives is adapted to drive said brush attachment in an oscillating motion.

10. A method for removing articular cartilage fragments comprising the steps of:
    providing a cartilage fragment removal device comprising:
       a shaft having a proximal end and a distal end and dimensioned to be inserted into an incision of the size made for insertion of surgical instruments during arthroscopic surgery;
       a brush attachment having a plurality of bristles thereon coupled to said distal end of said shaft; and
       drive means coupled to a proximate end of said shaft for driving said brush attachment;
    making an incision in a portion of a body for permitting access to an area having an articular cartilage fragment to be removed;
    inserting into said incision said brush attachment;
    driving said brush attachment;
    bringing said brush attachment in a driving condition into contact with said articular cartilage fragment to be removed until said articular cartilage fragment is detached; and
    removing said detached articular cartilage fragment from said body.

11. The method of claim 10 wherein said bristles are arranged in a substantially four-sided orientation.

12. The method of claim 11 wherein said bristles are arranged in a substantially rectangular orientation.

13. The method of claim 10 wherein said bristles extend at a substantially ninety degree angle from said shaft.

14. The method of claim 10 further comprising a suction conduit having a proximal end and a distal end wherein said distal end is proximate said brush attachment.

15. The method of claim 10 wherein said drive means drives is adapted to drive said brush attachment in an oscillating motion.

16. A method for removing articular cartilage fragments comprising the steps of:
    providing a cartilage fragment removal device comprising:
       a shaft having a proximal end and a distal end and dimensioned to be inserted into an incision of the size made for insertion of surgical instruments during arthroscopic surgery;
       a brush attachment having a plurality of bristles thereon coupled to said distal end of said shaft, said bristles are arranged in a substantially circular orientation; and
       drive means coupled to a proximate end of said shaft for driving said brush attachment;
    making an incision in a portion of a body for permitting access to an area having an articular cartilage fragment to be removed;
    inserting into said incision said brush attachment;
    driving said brush attachment;
    bringing said brush attachment in a driving condition into contact with said articular cartilage fragment to be removed until said articular cartilage fragment is detached; and
    removing said detached articular cartilage fragment from said body.

17. A method for removing articular cartilage fragments comprising the steps of:
    providing a cartilage fragment removal device comprising:
       a shaft having a proximal end and a distal end and dimensioned to be inserted into an incision of the size made for insertion of surgical instruments during arthroscopic surgery;
    a brush attachment having a plurality of bristles thereon coupled to said distal end of said shaft, said bristles extend parallel to an axis of said shaft; and
    drive means coupled to a proximate end of said shaft for driving said brush attachment;
    making an incision in a portion of a body for permitting access to an area having an articular cartilage fragment to be removed;
    inserting into said incision said brush attachment;
    driving said brush attachment;
    bringing said brush attachment in a driving condition into contact with said articular cartilage fragment to be removed until said articular cartilage fragment is detached; and
    removing said detached articular cartilage fragment from said body.

18. A method for removing articular cartilage fragments comprising the steps of:
    providing a cartilage fragment removal device comprising:
       a shaft having a proximal end and a distal end and dimensioned to be inserted into an incision of the size made for insertion of surgical instruments during arthroscopic surgery;

a brush attachment having a plurality of bristles thereon coupled to said distal end of said shaft; and drive means coupled to a proximate end of said shaft for driving said brush attachment, said drive means is adapted to drive said brush attachment in a rotary motion;

making an incision in a portion of a body for permitting access to an area having an articular cartilage fragment to be removed;

inserting into said incision said brush attachment;

driving said brush attachment;

bringing said brush attachment in a driving condition into contact with said articular cartilage fragment to be removed until said articular cartilage fragment is detached; and removing said detached articular cartilage fragment from said body.

* * * * *